United States Patent
Lowe

[11] Patent Number: 6,026,959
[45] Date of Patent: Feb. 22, 2000

[54] PROTECTIVE KIT FOR MEDICAL SHARPS AND METHOD FOR USING SAME

[75] Inventor: Kim H. Lowe, Orem, Utah

[73] Assignee: Protec Medical Corporation, Orem, Utah

[21] Appl. No.: 09/089,031

[22] Filed: Jun. 2, 1998

Related U.S. Application Data

[63] Continuation-in-part of application No. 08/681,220, Jul. 22, 1996, Pat. No. 5,758,775.

[51] Int. Cl.$^7$ ...................................................... B65F 83/10
[52] U.S. Cl. ........................... 206/571; 206/365; 206/523
[58] Field of Search .................................... 206/570, 571, 206/363, 364, 365, 380, 523, 461, 467, 565

[56] References Cited

U.S. PATENT DOCUMENTS

| | | | |
|---|---|---|---|
| 3,625,353 | 12/1971 | Ishii ......................................... | 206/365 |
| 4,936,449 | 6/1990 | Conrad et al. ........................... | 206/366 |
| 5,133,454 | 7/1992 | Hammer . | |
| 5,145,063 | 9/1992 | Lee .......................................... | 206/364 |
| 5,156,267 | 10/1992 | Yates, Jr. et al. ........................ | 206/365 |
| 5,353,935 | 10/1994 | Yeager et al. ............................ | 206/813 |
| 5,407,070 | 4/1995 | Bascos et al. ............................ | 206/365 |
| 5,607,403 | 3/1997 | Kretzschmar et al. .................. | 206/365 |
| 5,769,223 | 6/1998 | Marsh ...................................... | 206/365 |

Primary Examiner—Bryon P. Gehman
Assistant Examiner—Luan K. Bui
Attorney, Agent, or Firm—Thorpe, North & Western LLP

[57] ABSTRACT

A one-time resealable protective kit for medical sharps has a stiff body which has a predetermined shape for initially packaging a medical sharps and for receiving the used medical sharp. The stiff body is designed so as to prevent the blade or needle of the medical sharps from piercing the stiff body. The protective kit has a resealable cover and a lower attachment mechanism that can be used to affix the protective kit to a table or other suitable surface. In operation, the protective kit is releasably secured to a table or other suitable surface by contacting the attachment mechanism to the surface. The user then peels back the cover of the protective kit to access the medical sharp. Once the medical sharp has been used, it is replaced into the body of the protective kit. The cover can then be closed over the body of the protective kit, effectively sealing the medical sharp inside the protective kit. The entire protective kit can then be safely disposed of in accordance with standard medical practices.

9 Claims, 4 Drawing Sheets

PROTECTIVE KIT FOR MEDICAL SHARPS AND METHOD FOR USING SAME

This is a continuation-in-part of application Ser. No. 08/681,220 filed on Jul. 22, 1996 U.S. Pat. No. 5,758,775.

BACKGROUND

1. Technical Field

The present invention relates to packaging for medical sharps. More particularly, the present invention relates to a one-time use container which allows a user to safely store and dispose of medical sharps.

2. Background Art

The term "medical sharps" is generally defined as medical instruments having a sharp cutting edge or sharp point. In the medical environment, sharps include hypodermic needles, scalpel blades, and the like. Handling of medical sharps is a well known hazard for medical personnel because medical sharps may easily subject medical personnel to cuts, abrasions, puncture wounds or needle sticks when being handled, especially when being removed from their packaging or while being disposed of Disposal procedures can involve a significantly increased risk of cuts or puncture wounds when excessive handling of the medical sharps is required. It is also well known that biomedical hazards, such as exposure to the HIV virus, are associated with the handling of used medical sharps.

Cuts, needle sticks or abrasions may subject medical personnel performing disposal of medical sharps to potentially fatal diseases and possibly an expensive and painful treatment regimen. In addition, hospitals and other care providers face legal exposure and enormous liability for employees who are inadvertently exposed to the above-described hazards which are inherently associated with accidental cuts or puncture wounds.

Accordingly, there is a well-identified need in the health care industry for protective packaging for distributing and disposing of medical sharps. Recognizing the need for safe packaging, several inventors have addressed the problem and offered potential solutions.

For example, U.S. Pat. No. 5,407,070 to Bascos et al. discloses a one-time resealable package for needled medical devices which utilizes an arrow-shaped portion to seal a used needled medical device inside the dispensing container. While this is a desirable end, the package as taught by Bascos et al. requires the user to excessively manipulate the package in order to reseal it and achieve the stated goal. The package is not simple to use and cannot be opened and closed with only one hand. In addition, the plastic material described by Bascos et al. is, in itself, not strong enough to withstand penetration by a needled medical device.

Another patent, U.S. Pat. No. 5,385,105 to Conard et al., shows the use of a Styrofoam block for securing medical sharps and other medical instruments as part of the disposal process. This patent also shows the use of an adhesive strip to secure the medical sharps disposal block to the surface of a table or other suitable surface. This device, however, is designed for storing multiple needled medical devices and also requires a separate snap-on lid for securing the needled medical devices inside the container. Using a single device to store multiple needled medical devices presents a continuing danger because the proliferation of needles presents an increased risk of accidental needle sticks from the accumulated needled medical devices.

U.S. Pat. No. 5,024,326 to Sandel et al. discloses a container that uses reticulated foam to protect the user from accidentally contacting the tips of needles and other medical instruments. This invention is fairly complex and requires the user to manipulate two body halves in order to open and close the container. In addition, this container is designed to contain multiple medical sharps and is not a viable solution for shipping and ultimately disposing of a single needled medical sharp in its own container.

U.S. Pat. No. 5,385,105 to Withers et al. discloses a medical sharps disposal system that allows for the collection of multiple used needles in a single container. After the container is full, the entire container can be collected with other similar containers and then the containers can be incinerated. Once again, this method is relatively costly and increases the risk of exposure due to maintaining a single receptacle for multiple used needled medical devices.

While the above described devices attempt to address the problem of medical sharps disposal, they lack cost effectiveness, simplicity of manufacture and ease of operation. What is needed, therefore, is a one-time use container for an individual medical sharp that can be used to safely distribute and dispose of medical sharps. Further, the container should be inexpensive and simple to use. The container should be able to be manipulated with one hand in order to facilitate the careful handling of the medical sharp stored within the container, thereby reducing the probability of an accidental cut, puncture wound or needle stick. Finally, the user of the protective container should be able to dispose of the used medical sharp and the container in a standard hospital medical sharps receptacle.

DISCLOSURE OF INVENTION

The present invention is a self-contained one-time use package for distributing and disposing of medical sharps which affords simplicity of manufacture, cost effectiveness, assurance of sterility, easy and safe opening and resealing of the package in conjunction with safe handling of the medical sharps, and other advances.

In operation, a user grasps the protective kit in one hand and the cover of the bottom adhesive layer in the other hand and peels the cover from the body until the adhesive attachment strip is exposed. The user can then secure the protective kit to a nearby table or other suitable surface. The user then peels back the upper sealed layer to expose the medical sharp. The user then carefully removes the medical sharp from the protective kit. After the medical sharp has been used, the user can safely embed the blade or needle portion of the medical sharp in the base material, thereby isolating the blade or needle and preventing an accidental cut or needle stick. The user then reseals the upper adhesive strip to completely enclose the medical sharp. The entire protective kit can then be discarded into a standard hospital medical sharps disposal container.

Accordingly, it is an advantage of the present invention to provide a cost effective, simple to manufacture, and easy to use protective kit for medical sharp.

It is another advantage of the present invention to provide a protective kit for an individually packaged medical sharp that can be used to safely distribute and dispose of medical sharp such as scalpels, hypodermic needles and standard intra-venous (I.V.) catheters.

It is a further advantage of the present invention to provide a protective kit which can be manipulated with one hand in order to facilitate the careful handling of the medical sharp, thereby reducing the probability of an accidental cut or needle stick.

In addition, it is yet another advantage of the present invention to provide a protective kit for a medical sharp that can be disposed of in a standard hospital receptacle.

Other novel features which are believed to be characteristic of the invention, together with further objects and advantages thereof, will be better understood from the following detailed description considered in connection with the accompanying drawings in which a preferred embodiment of the invention is illustrated by way of example. It is to be understood, however, that the drawings are for the purpose of illustration and description only, and are not intended as a definition of limits of the invention.

BEST MODE FOR CARRYING OUT THE INVENTION

Figure 1:
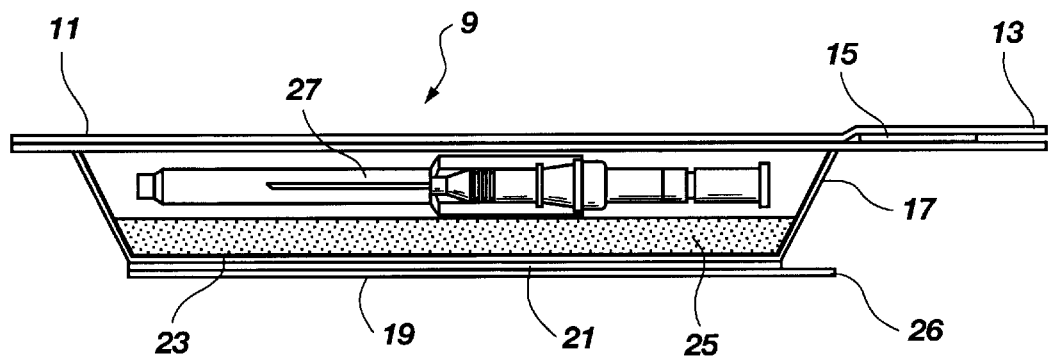
FIG. 1 shows a side cross-sectional view of a sealed protective kit in accordance with the preferred embodiment, packaged with a standard I.V. catheter resting on the base material.

Referring to FIG. 1, a protective kit 9 in accordance with a preferred embodiment of the present invention includes a medical sharp 27 and a protective container 11. Prior to using medical sharp 27, it is sealed within protective container 11. Medical sharp 27 may be any device that includes a blade, a cutting edge, or one or more needles. For convenience of illustration and purposes of explanation, the Figures herein show medical sharp 27 as a standard I.V. catheter as one example of a suitable medical sharp that could be used in accordance with the present invention. This illustration should not be construed as a limitation. For the sake of clarity, the discussion below refers to a catheter 27, recognizing that catheter 27 is only one suitable medical sharp within the scope of the present invention.

Protective container 11 includes an adhesive peel-back sealed cover 13, a resealing pad 15, a body 17, a lower adhesive strip cover 19, a lower adhesive strip 21, a protective layer 23, a base material 25, and a tab portion 26. Peel-back cover 13 is a flexible material that covers the top portion of protective container 11, and that can be completely or partially removed to provide access to catheter 27 stored within protective container 11. Resealing pad 15 is a soft material that sticks to peel-back cover 13 using an adhesive. The force joining adhesive peel-back cover 13 to resealing pad 15 is overcome when peel-back cover 13 is peeled back to expose catheter 27. Once catheter 27 has been used and returned to protective container 11, peel-back cover 13 is then sealed to resealing pad 15 to seal the used needled device 27 inside protective container 11.

Body 17 is constructed of a durable, structurally strong material, preferably a stiff, see-through plastic. In the preferred embodiment, Lexan is formed by a vacuum process, resulting in a body 17 that is 0.020 to 0.030 thick. Body 17 provides a cavity that is shaped to receive needled device 27. Body 17 is lined with protective layer 23 to resist punctures by catheter 27. Protective layer 23 may be any suitable material that resists punctures, including metal, wire mesh, and various types of plastic, and may be located on the interior or exterior of body 17. While the preferred embodiment herein uses a metal layer for protective layer 23, other materials are equally within the scope of the present invention. For example, a body 17 may provide a protective layer 23 of plastic by simply forming body 17 with a thickness sufficient to resist punctures by catheter 27. Whatever the specific construction, the present invention encompasses any protective layer, whether attached to body 17 or fabricated integral to body 17, that will resist puncture by medical sharps.

Lower adhesive strip 21 is a relatively flat piece of double-sided adhesive material, such as double-sided foam tape. One side of lower adhesive strip 21 is attached to the bottom of plastic body 17, while the other side of lower adhesive strip 21 is covered by lower adhesive strip cover 19. Lower adhesive strip cover 19 includes a tab portion 26 that allows a person to remove adhesives strip cover 19 from adhesive layer 21 by pulling on tab portion 26.

The preferred embodiment includes lower adhesive strip 21, but the present invention extends to any type of releasable attachment mechanism that can serve to attach protective container 11 to some surface, whether the attachment mechanism is adhesive, magnetic, or any other type of releasable attachment mechanism.

Base material 25 is preferably a dense foam material capable of retaining the sharp point of any medical sharp with sufficient retention force to keep the medical sharp in place once its sharp point or edge is embedded in base material 25. While base material 25 is a layer of foam in the preferred embodiment herein, any material capable of receiving and retaining a sharp point or edge of a medical sharp is within the scope of the invention disclosed herein.

Figure 2:
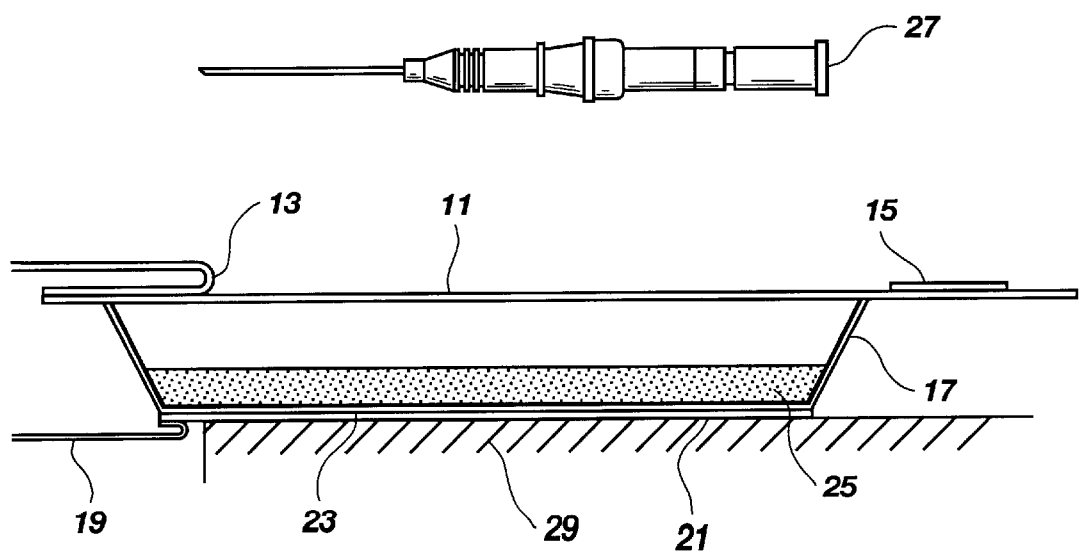
FIG. 2 shows a side cross-sectional view of the protective kit of FIG. 1 after being affixed to a stable surface, with the I.V. catheter removed.

Referring now to FIG. 2, adhesive layer 21 is exposed by pulling on tab portion 26 to remove lower adhesive strip cover 19. Protective container 11 is affixed to surface 29 and adhesive peel-back cover 13 is peeled back to allow removal of catheter 27 from protective container 11. Catheter 27 is then ready for use.

Figure 3:
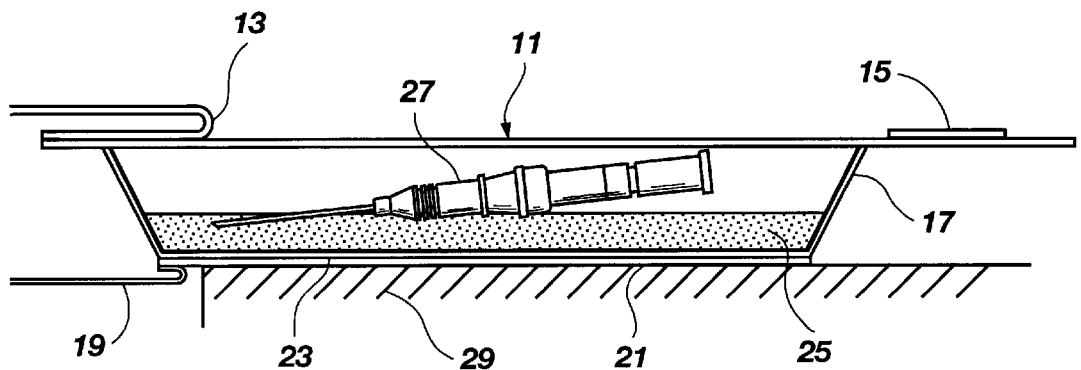
FIG. 3 shows a side cross-sectional view of the protective kit of FIG. 1 affixed to a stable surface with the I.V. catheter needle inserted into the base material after being used.

Referring now to FIG. 3, after catheter 27 has been used, it is reinserted into protective container 11 with the needle portion embedded into base material 25, effectively preventing any undue exposure to the contaminated needle of catheter 27. Base material 25 obviates the need for a protective cap on the needle portion of catheter 27. As a result, cost savings can be expected with respect to conventional packaging, which generally must include a removable cap for the needle. In addition, the protective needle kit offers enhanced safety for the user, since there is no cap to replace after catheter 27 has been used.

Figure 4:
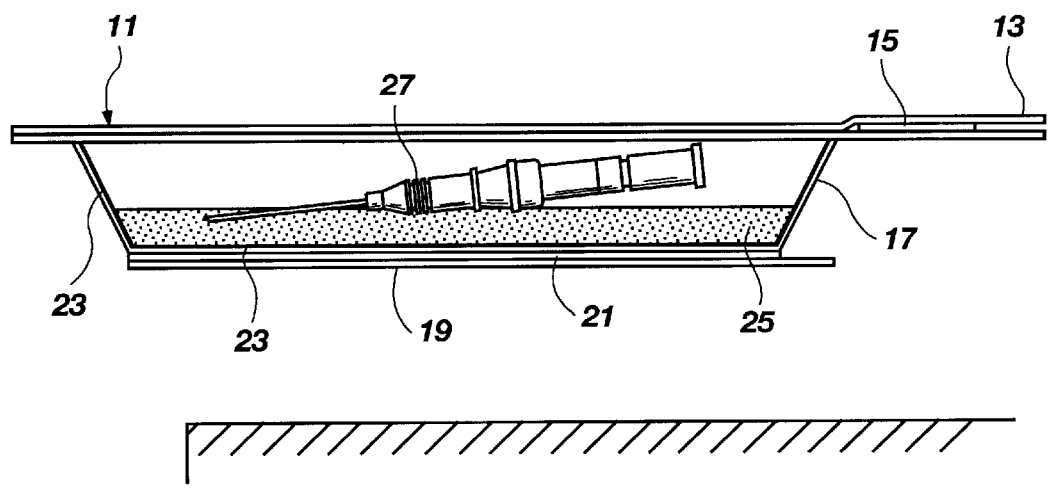
FIG. 4 shows a side cross-sectional view of the protective kit of FIG. 1 with the I.V. catheter needle inserted into the base material after being used, with the protective kit being resealed and ready for disposal.

Referring now to FIG. 4, after the needle portion of used catheter 27 has been embedded into base material 25, the adhesive peel-back cover 13 is resealed over the protective container 11 by adhering pull-back cover 13 to resealing pad 15. This effectively seals catheter 27 inside protective container 11. At this point, protective container 11 is removed from surface 29 and lower adhesive strip cover 19 is then returned to its original position covering lower adhesive strip 21. Protective container 11 is then ready for disposal. The lower adhesive strip 21 is releasably attached to surface 29. The force of attachment is sufficient to keep protective container 11 from being easily dislodged. The force of attachment can be overcome by lifting protective container 11 with a steady upward force.

Figure 5:
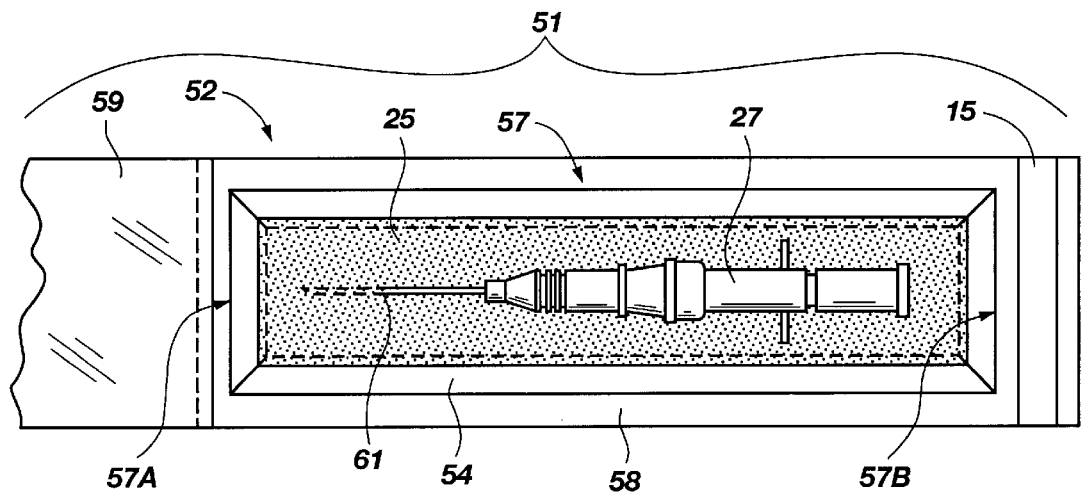
FIG. 5 is a top plan view of a new first alternative preferred embodiment of the protective kit having the top peeled back from the body to expose the opening.
Figure 6:
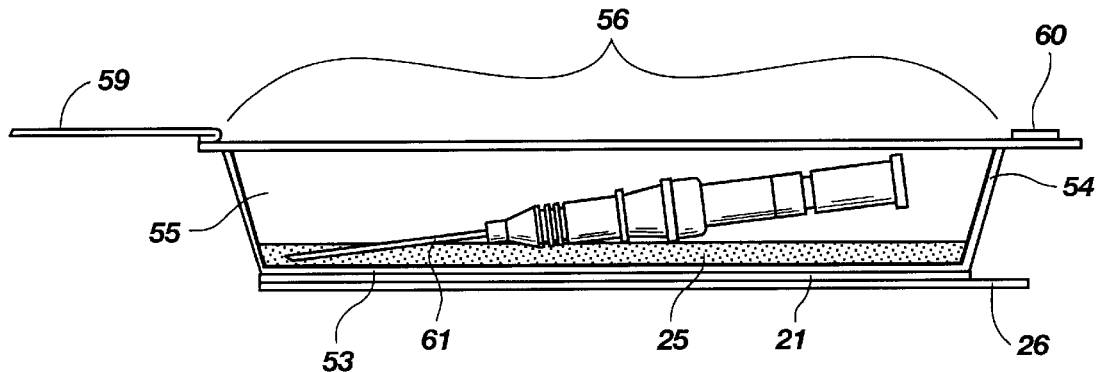
FIG. 6 is a see-through side elevational view of the new first alternative preferred embodiment of the protective kit having an adhesive layer on the outer surface of the bottom portion covered by an adhesive strip cover.
Figure 7:
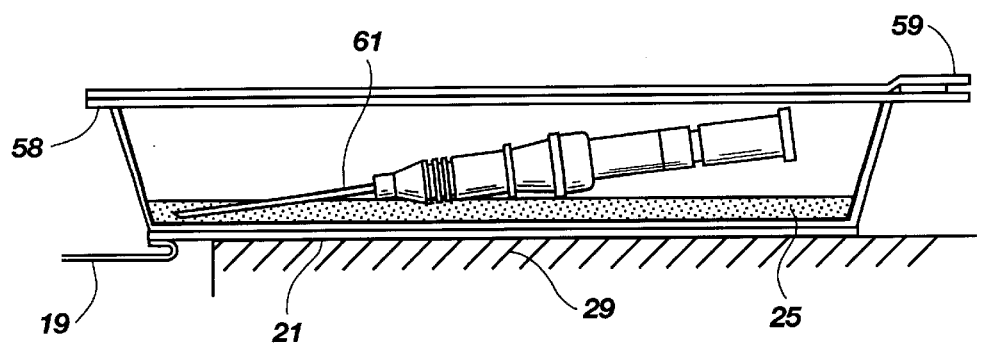
FIG. 7 is a see-through side elevational view of the new first alternative preferred embodiment of the protective kit showing the adhesive layer on the outer surface of the bottom portion adhered to a work surface.

A new first alternative preferred embodiment of the protective container kit 51 is shown in FIGS. 5 through 7. The protective container kit 51 is also referred to herein as a one-time-usable resealable receptacle for medical sharps. Referring now to FIGS. 5, 6 and 7, the body 52 of the new preferred embodiment container kit 51 is hot stamped from a sheet of high-density polystyrene plastic having a thickness of approximately 0.75 millimeter (about 0.030 inch). Polystyrene plastic of this thickness is difficult to cut or puncture with the sharps typically associated with medical use. Thus, no protective reinforcing layer is required in combination with the material from which the body is fabricated. Other polymer plastic materials having similar resistance to cutting and puncturing may be substituted for polystyrene. The body 52 has a bottom portion 53 and a wall portion 54 continuous with and surrounding said bottom portion 53, said bottom portion 53 and said wall portion 54 having inner and outer surfaces, the inner surfaces defining a chamber 55 for receiving a medical sharp 27, the chamber 55 having an opening 56 defined by an upper edge 57 of the wall portion 54. A foam layer 25 is applied to the inner surface of bottom portion 53. The foam layer 25 is suited to receive and frictionally retain the medical sharp 27. The body 52 includes a flange portion 58 which surrounds the opening 56. A cover 59 is permanently attached to the flange portion 58 along a first portion 57A of the upper edge 57. A releasable adhesive layer 60 is applied to the flange portion 58 along a second portion 57B of the upper edge 57 opposite the first portion 57B. The cover 59 may be releasably adhered to adhesive layer 60 in order to close the opening 56. The needle 61 of a used medical sharp 27 is shown embedded within the foam layer 25. The function of the exposable adhesive layer 21, the lower adhesive strip cover 19 and the tab 26 at the end of adhesive strip cover 19 have been heretofore described.

Figure 8:
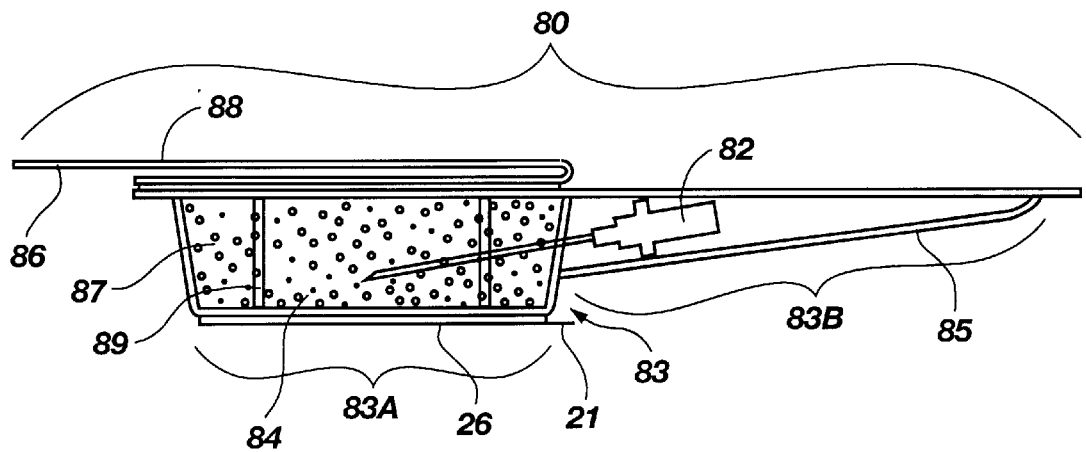
FIG. 8 is a see through side elevational view of a new second alternative preferred embodiment of the protective kit having the top peeled back from the body to expose a portion of the opening.
Figure 9:
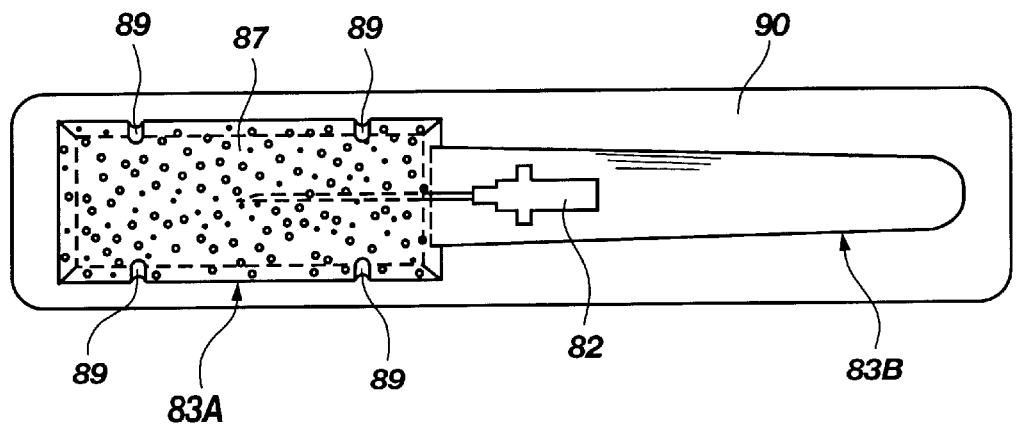
FIG. 9 is a top plan view of the new second alternative preferred embodiment of the protective kit having the top removed from the body altogether.

A new second alternative preferred embodiment of the protective container kit 80 is shown in FIGS. 8 and 9. The protective container kit 80 is also referred to herein as a one-time-usable resealable receptacle for medical sharps. This second new embodiment is particularly adapted to safeguard catheter needles 82 after use. Referring now to FIG. 8, the body 83 of the new preferred embodiment container kit 80 is hot stamped from a sheet of puncture resistant high-density polystyrene plastic having a thickness of approximately 0.75 millimeter (about 0.030 inch). The body has a first chamber 83A which adjoins a second chamber 83B. The first chamber 83A contains a block of foam 87. The first chamber 83A has four reinforcing ribs 89 molded therein, two of which are visible in this view. A flexible cover 88 is bonded to the portion of flange 90 which surrounds chamber 83A such that it is difficult to remove therefrom. A releasable adhesive layer 88 is deposited either on the portion of flange 90 which surrounds the second chamber 83B or on the portion of the cover 86 which fits over the second chamber 83B. Thus, a health care service provider can peel back the cover 86 only far enough to expose the second chamber 83B and the face of the foam block 87 where the second chamber 83B adjoins the first chamber 83A. After the catheter needle 82 has been used, the sharp point thereof is slid down the floor 85 of second chamber 83B until it contacts and pierces the foam block 87. The needle 82 is frictionally held in place by the foam. Once the sharp point of needle 82 has been inserted into the foam block 87, the cover may be folded to its original position and adhered to the portion of flange 90 which surrounds the second chamber 83B.

From the foregoing, it will be appreciated that, although certain embodiments of the invention have been described herein for purposes of illustration, various modifications may be made without deviating from the spirit and scope of the invention. For example, the overall size and shape of the protective container could be adapted to accommodate various sizes and shapes of medical sharps. In addition, the various components of the protective container could be made from various different materials. Particularly, the protective inner lining need not be made of metal but may be constructed of any suitable puncture-resistant material. Accordingly, the invention is not limited except by the appended claims.

What is claimed is:

1. A one-time-usable resealable receptacle for storing a medical device having a sharp element for cutting or piercing tissue, said receptacle comprising;

a body having first and second interconnected chambers, a flange surrounding both chambers, and an opening defined by an inner peripheral edge of said flange, the first and second chambers having different depths with the first chamber being deeper than the second chamber and configured for receiving said sharp element, the second chamber having a floor higher than a floor of the first chamber;

a foam block disposed in said first chamber, said foam block frictionally retaining said sharp element when pierced thereby;

a cover which is permanently attached to a first portion of said flange which surrounds said first chamber except where said first chamber is interconnected with said second chamber, and which releasably attaches to a second portion of said flange which surrounds said second chamber except where said second chamber is interconnected with said first chamber, said cover, when unattached to said second portion of said flange, providing access to said second chamber and, when attached to said second portion of said flange, limiting access to said second chamber.

2. The one-time-usable resealable receptacle of claim 1, wherein said body is formed from polystyrene plastic.

3. The one-time-usable resealable receptacle of claim 1, wherein said first chamber has inner and outer surfaces, said inner surface being in contact with said foam block, and said receptacle further comprises at least one double-sided adhesive layer having a first side thereof adhered to a bottom portion of said outer surface of said bottom portion and a second side thereof releasably covered by a protective film which may be removed to provide releasable attachment of the receptacle to work surfaces.

4. The one-time-usable resealable receptacle of claim 1, wherein said body incorporates at least one reinforcing rib.

5. The one-time-usable receptacle of claim 1, wherein said cover releasably attaches to said second portion of said flange with adhesive that is applied to said cover.

6. A one-time-usable resealable receptacle of claim 1, wherein said body is sized to receive an individual medical device.

7. A one-time-usable resealable receptacle of claim 1, wherein said floor of said second chamber has a minimum thickness of about 0.75 millimeter.

8. A one-time-usable resealable receptacle of claim 1, wherein said floor of said second chamber is sloped towards the first chamber.

9. A one-time-usable resealable receptacle of claim 1, wherein said floor of said second chamber is disposed alongside the foam block such that said sharp element of said medical device may be slid down said floor and into said foam block.

* * * * *

UNITED STATES PATENT AND TRADEMARK OFFICE
CERTIFICATE OF CORRECTION

PATENT NO. : 6,026,959
DATED : February 22, 2000
INVENTOR(S) : Kim H. Love

It is certified that error appears in the above-identified patent and that said Letters Patent is hereby corrected as shown below:

On the title page, item [73] Assignee, "Protec" should read --Protex--.

Signed and Sealed this

Thirteenth Day of February, 2001

Attest:

NICHOLAS P. GODICI

Attesting Officer

Acting Director of the United States Patent and Trademark Office